(12) United States Patent
Chaganti et al.

(10) Patent No.: US 6,309,860 B1
(45) Date of Patent: Oct. 30, 2001

(54) CLONING AND USES OF BCL-8

(75) Inventors: Raju S. K. Chaganti, New York, NY (US); Vadim Dyomin, Tenafly, NJ (US); Riccardo Dalla-Favera, New York, NY (US)

(73) Assignees: The Trustees of Columbia University in the City of New York; Sloan-Kettering Institute for Cancer Research, both of New York, NY (US)

( * ) Notice: Subject to any disclaimer, the term of this patent is extended or adjusted under 35 U.S.C. 154(b) by 0 days.

(21) Appl. No.: 09/450,852

(22) Filed: Nov. 29, 1999

Related U.S. Application Data

(63) Continuation of application No. PCT/US98/10734, filed on May 27, 1998.
(60) Provisional application No. 60/047,673, filed on May 27, 1997.

(51) Int. Cl.[7] .......................... C07H 21/04; C12N 15/63; C12N 15/00; C12N 21/00
(52) U.S. Cl. ................. 435/69.1; 435/70.1; 435/71.1; 435/471; 435/455; 435/325; 435/252.3; 435/320.1; 536/23.1; 536/23.5; 536/24.31
(58) Field of Search .................. 435/69.1, 71.1, 435/70.1, 471, 455, 325, 252.3, 320.1; 536/23.1, 23.5, 24.31

(56) References Cited

FOREIGN PATENT DOCUMENTS

94/29343    12/1994  (WO) .

OTHER PUBLICATIONS

Clontech Catalog. p. 214, 1993/1994.*
Hillier et al. Jul. 1995. GenBank Accession No. H20348.*
Chaganti, R.S.K., "New Insights into the genetics on non–Hodgkin's Lymphoma", *Int. Proc. J.* 5:34–41 (1998). (Exhibit 2).
Chaganti, S.R. et al., "Involvement of BCL6 in Chromosomal Aberrations Affecting Band 3q27 in B–Cell Non–Hodgin Lymphoma", *Genes, Chromosomes & Cancer* 23: 323–327 (1998). (Exhibit 3).
Cigudosa, J.C., et al., "Cytogenetic Analysis of 363 Consecutively Ascertained Diffuse Large B–Cell Lymphomas", *Genes, Chromosomes & Cancer* 25:123–133 (1999). (Exhibit 4).
Dyomin V.G. et al. Cloning of the BCL8 gene involved in chromosomal translocations affecting band 15q11–13 in diffuse large–cell lymphomas. *Blood*. Dec. 1996, 10: 632A, Abstract 2518. (Exhibit 5).
Dyomin, V.G., et al., "BCL8, a novel gene involved in translocations affecting band 15q11–13 in diffuse large–cell lymphoma", *Proc. Natl. Acad. Sci. USA* 94: 5728–5732 (1997). (Exhibit 6).
Iida, S. et al., "Deregulation of MUM1/IRF4 by chromosomal translocation in multiple myeloma" *Nature Genetics* 17:226–229 (1997). (Exhibit 7).
Levine E.G. et al. "Four new recurring translocations in non–Hodgkin lymphoma." *Blood*. Oct. 1989, vol. 74(5) : 1796–1800, see entire document. (Exhibit 8).
Rao, P.H. et al., "Chromosomal and Gene Amplification in Diffuse Large B–Cell Lymphoma", *Blood* 92: 234–240 (1998). (Exhibit 9).

* cited by examiner

*Primary Examiner*—Carla J. Myers
(74) *Attorney, Agent, or Firm*—John P. White; Cooper & Dunham LLP

(57) ABSTRACT

This invention provides an isolated nucleic acid which encodes bcl-8. This invention also provides an oligonucleotide of at least 15 nucleotides capable of specifically hybridizing with a sequence of nucleotides within a nucleic acid which encodes bcl-8. Further, this invention provides an agent capable of blocking the expression of BCL-8. This invention also provides various methods of determining whether a subject is afflicted with diffuse large cell lymphoma. This invention further provides a method of determining whether a subject has a predisposition for diffuse large cell lymphoma. This invention further provides various methods of treating a subject afflicted with diffuse large cell lymphoma. This invention also provides various methods of preventing diffuse large cell lymphoma in a subject. This invention also provides pharmaceutical compositions for treating and/or preventing diffuse large cell lymphoma.

15 Claims, 10 Drawing Sheets

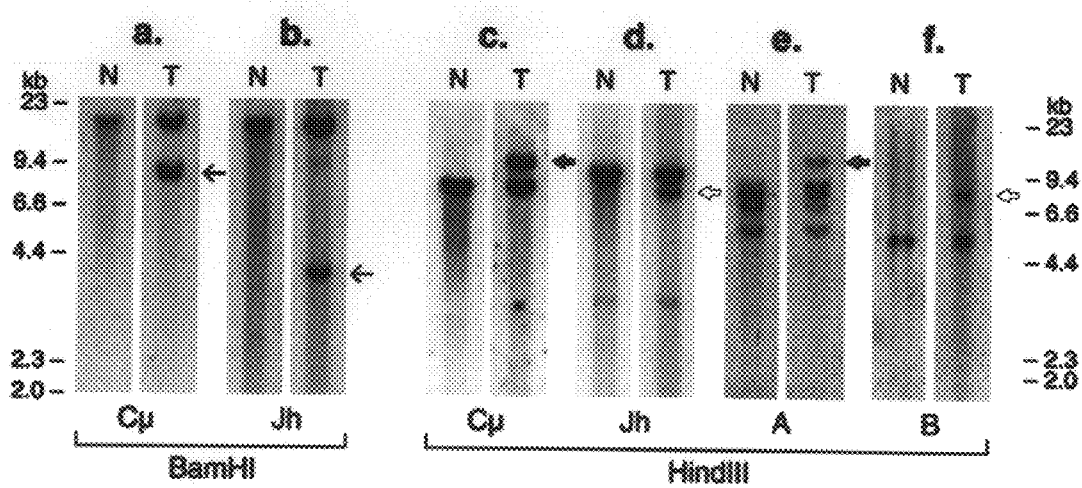

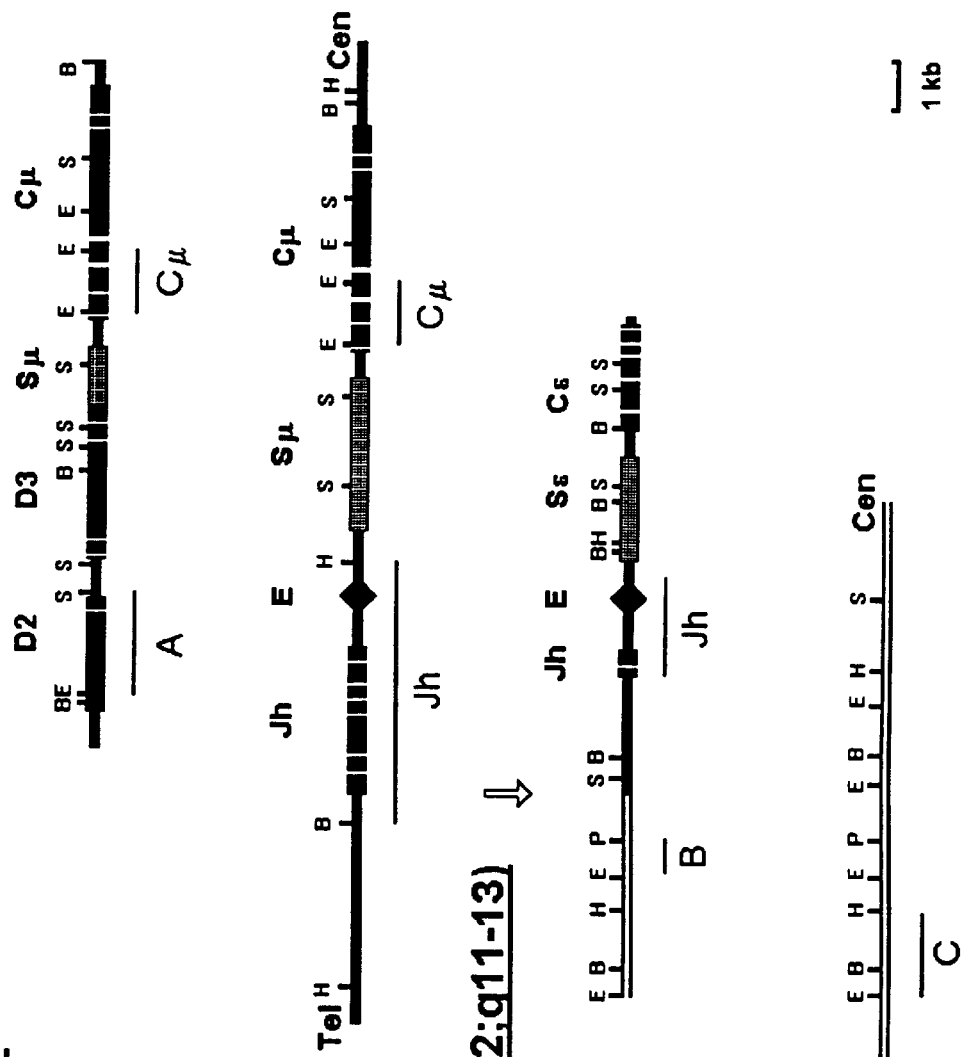
FIGURE 2 I. Deleted IGH allele
FIGURE 2 II. Chromosome 14
FIGURE 2 III. der(14)t(14;15)(q32;q11-13)
FIGURE 2 IV. Chromosome 15

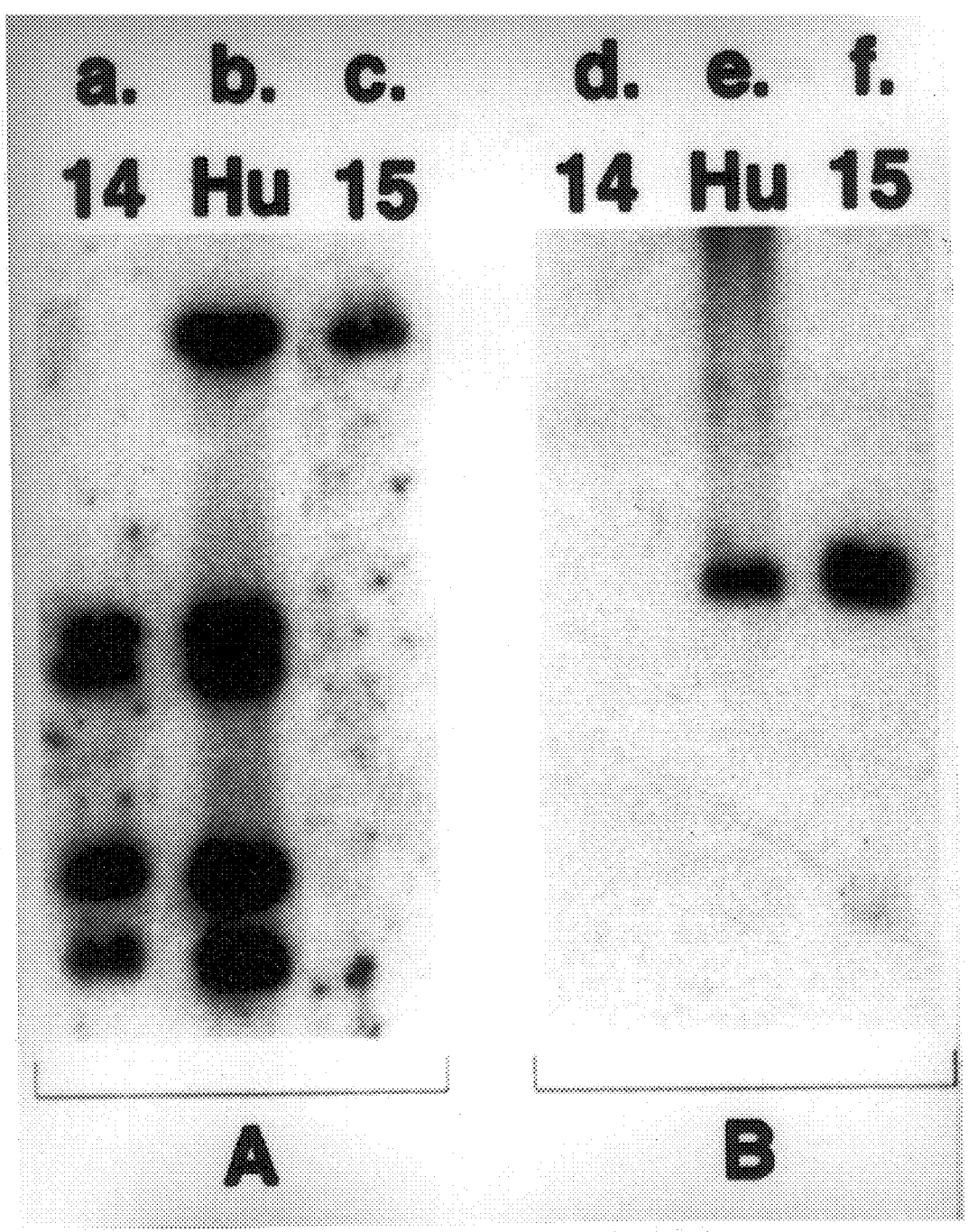

FIGURE 8A

```
             10         20         30         40         50         60
5' ACCACTATAC GGCTCGAGCG GCCGCCCGGG CAGGTCTGTA CTTTACATGC AGTGCTACTC
             70         80         90        100        110        120
   TTTCGGCATT CCTGGTTGAA CTACTTAAAA GTTCAGTAGC CATGCAAGAA CAGGTGCTGG
            130        140        150        160        170        180
   GTGGAAAACG CTTTTTAGTT ATTGGCTATT TACTTGAAAA GTCATCAAGA GTTCATATAA
            190        200        210        220        230        240
   CTAGACCTGT CTTGGAGCAA TTTTTATCTT TTGCAAAATA CCTTGATGGT TTATCTCATG
            250        260        270        280        290        300
   GAGCACCTTT GCTGAAGCAG CTTTGTGATC ATATTTTGTT TATTAACCCA GCCATCTGGA
            310        320        330        340        350        360
   TACATACACC TGCAAAGGTT CAACTTTCCC TATATACATA TTTGTCTGCT GAATTTATTG
            370        380        390        400        410        420
   GAACTGCTAC CATCTACACC ACCATACGCA GAATAGGACA GTTATTAAAG ATAATGCACA
            430        440        450        460        470        480
   CCTTAAAATA TTACTACTGG GTTATTAATC CTGCTGACAG TAGCGGCATT ACACCTAAAG
            490        500        510        520        530        540
   GATTAGAGCC AAAGATTCCT GAAGACAGAG CTGATGCCAT GTACTCAAGT GGGTCTCTGC
            550        560        570        580        590        600
   CTCTCAGAGG TGGCCTTGGT CTTCAAGTTT CAGCAATTCT GGGAAGCCAA GGACACCTCC
            610        620        630        640        650        660
   ATCTCCTCCT GCCTGATCTG CAACTCATCT GAGAGCAGCT TTCTCATTGG AATGTCTTGT
            670        680        690        700        710        720
   GTTTAAGGAA CAAGAATCCC TGTTTCCGGT TTGGGTGCCC AAGTGCACCT ACTGGATCCA
            730        740        750        760        770        780
   ACCCAGGATT GGAGATACTT TGCAGAACAC AACATCATCT GGCACATGAC CAGCCATGGT
            790        800        810        820        830        840
   GTTTCACTTT CACAATTTCA GCTTCCTTCA CTGATGGCAG CATAATCGTG GTTCAGCAGC
            850        860        870        880        890        900
   CTCCAAGACC AGGGGCTGGT GTGGGCGGCT ACAGGGAGAA ATTGAAGAGG AAGTTCTTGG
            910        920        930        940        950        960
   TGGTGCCCTC CATGAGTACA AAGAAGCCTC ACAGTCCCCA GGACACCCTT CCGTGCATGG
            970        980        990       1000       1010       1020
   TGTCACTGAC ATCTTTATTT CTTTTGTCAC GTTCTGTAAA TCACAATGAA TGGGGTATTC
           1030       1040       1050       1060       1070       1080
   TTCTTCTATT ATATATTTGT TAAGTCTTTT TTGGCATCTT TAAAAAAAAG TGGTAACTTT
           1090       1100       1110       1120       1130       1140
   ATCCTATGTA ATATCCCTGT TAAGTCCTAA AAGTCTTTTC TGATGTCTAT TTTGTCTGAA
```

FIGURE 8B

```
           1150       1160       1170       1180       1190       1200
      ATTTGCACAG CTACTATAGC TTTATTTCGG TTCATATTTT CATAATCCAT GTTTTCTCAT
           1210       1220       1230       1240       1250       1260
      CCTTTTATAT TTGTGAATGT GTAAAGTAAC TTTCTTGTGC ATAGCTAAGA GTTTGGTCTT
           1270       1280       1290       1300       1310       1320
      GCTTTTTTAA ATCGACTATA AGTTCTATTT TTAAACTAAT ATTTTCTCTT ATTTTTTGTT
           1330       1340       1350       1360       1370       1380
      TAAGATAGCA TTTCATAATG ATGTTTATTT CTCCATTAAC ATATTACCTA ATTCACTTTT
           1390       1400       1410       1420       1430       1440
      TATAAATATT ATATTTGTTA CCATAAGGTT TGCAAAAGGA GCGATTCTTC ATTTTGGAAC
           1450       1460       1470       1480       1490       1500
      CCTTTCTTAT TTTCTGGGTA CCATGAGAAA TTGTAGACTT TACTCCTATA TTCTCTTTCC
           1510       1520       1530       1540       1550       1560
      AAGCCCTAGG ATTAGCCATT TTTCCAAGAA ATGTTGCATA CCATTCTGCT ATGAAGGGAA
           1570       1580       1590       1600       1610       1620
      CCAAAACTCA AATCTTGATT CTGGGTGTAT TTTTTGTTAA TTTGCTGTCT TTTCTTGTAG
           1630       1640       1650       1660       1670       1680
      AACCTCTCAG GTAATGACTC TAGGAGGTAT GTGTTGTGTA TTAACCCATA TATACACACA
           1690       1700       1710       1720       1730       1740
      CATCTAAACT ATTTTTATTT AATTTTTATA CCTATATTAT GCTAAACTTG CAAATATATT
           1750       1760       1770       1780       1790       1800
      GACACATCTG CCCTGTTAAT ACCACATGAA TGTTTATTAC CTGCCTTCTA TTCCTGTCCC
           1810       1820       1830       1840       1850       1860
      TAACCTCGCA CTCCAACCGT GAGGAACCCC CTCCTGCCAC ACCCTGTCTA TTCCCTTTGT
           1870       1880       1890       1900       1910       1920
      AGTCCAGTTC CAGGATTTCT GTAGAGTGGA ACCAGATTGT GTATGTTTTG CTCTTTTGTG
           1930       1940       1950       1960       1970       1980
      GAACATCATC AGCTGGGGTA CAGTTCTGAC GTGCACTTTC TTTATTCTTT TATTGACTAC
           1990       2000       2010       2020       2030       2040
      ACTATTTCTG AGGTCACTTG GCACCTCTTC TGATTTCATA CATTTGTAAT GACATTAGAT
           2050       2060       2070       2080       2090       2100
      ATTTTCTATA TTGTCTGCAT TCTATCCTGG AATTCCTAAT CTCCTATTTA TTTATATTTT
           2110       2120       2130       2140       2150       2160
      TGTGAATTGG AATTAACCCT TTATGCTGTA TATTCTGTTG ATTTCAACAA ATTCATATCA
           2170       2180       2190       2200       2210       2220
      CATATTTACC ATTATAATAT TATACATAAT ACTTCCATCA CCCTTTTAAA TCTATTTTTT
           2230       2240       2250       2260       2270       2280
      ACCCATTTTC ATCATCTCCT TAAATTTCTC GCAAATACAG AATCACTTTG TGTGTTTGGA
           2290       2300       2310       2320       2330       2340
      CTTCTCCAGA ATATCAAATA AATAACATAT TATGTAGCTT TTTCAGACTT GTTTCTTTCA$_{3'}$
```

FIGURE 9

N- Met Gln Glu Gln Val Leu Gly Gly Lys Arg Phe Leu Val Ile Gly Tyr Leu Leu
                                        10                        30
Glu Lys Ser Ser Arg Val His Ile Thr Arg Pro Val Leu Glu Gln Phe Leu Ser
            40                                      50
Phe Ala Lys Tyr Leu Asp Gly Leu Ser His Gly Ala Pro Leu Leu Lys Gln Leu
                    60                                          70
Cys Asp His Ile Leu Phe Ile Asn Pro Ala Ile Trp Ile His Thr Pro Ala Lys
                            80                                        90
Val Gln Leu Ser Leu Tyr Thr Tyr Leu Ser Ala Glu Phe Ile Gly Thr Ala Thr
                                        100
Ile Tyr Thr Thr Ile Arg Arg Ile Gly Gln Leu Leu Lys Ile Met His Thr Leu
    110                                             120
Lys Tyr Tyr Tyr Trp Val Ile Asn Pro Ala Asp Ser Ser Gly Ile Thr Pro Lys
            130                                         140
Gly Leu Glu Pro Lys Ile Pro Glu Asp Arg Ala Asp Ala Met Tyr Ser Ser Gly
                    150                                         160
Ser Leu Pro Leu Arg Gly Gly Leu Gly Leu Gln Val Ser Ala Ile Leu Gly Ser
                        170
Gln Gly His Leu Leu His Leu Leu Pro Asp Leu Gln Leu Ile -C

CLONING AND USES OF BCL-8

This application is a continuation of PCT International Application No. PCT/US98/10734, filed May 27, 1998, designating the United States of America, which claims benefit of U.S. Provisional Application No. 60/047,673, filed May 27, 1997, the contents of which are hereby incorporated by reference into the present application.

The invention disclosed herein was made with Government support under Grant Nos. CA-34775, CA-66999 and CA-44029 from the National Institutes of Health of the United States Department of Health and Human Services. Accordingly, the United States Government has certain rights in this invention.

BACKGROUND OF THE INVENTION

Throughout this application, various publications are referenced in parentheses. Full citations for these publications may be found listed at the end of the specification. The disclosures of these publications in their entireties are hereby incorporated by reference into this application in order to more fully describe the state of the art as known to those skilled therein.

Recurrent chromosomal translocations recognized in the majority of lymphomas provide clues to mechanisms of lymphomagenesis. Immunoglobulin genes undergo specific rearrangements during differentiation of lymphoid cells and, errors in recombination lead to chromosome translocation and neoplastic transformation (Chaganti, R. S. K., 1991; Rabbits, T. H., 1994). Diffuse large cell lymphomas (DLCL) make up approximately 50% of non-Hodgkin lymphomas (Simon, R., et al., 1988) and show significant variability in terms of their pathologic manifestation, response to therapy and prognosis (Magrath, I., 1989). DLCL are also highly heterogeneous with respect to karyotypic abnormalities as well as underlying molecular lesions. So far, three genes have been identified whose normal pattern of expression is altered by a specific chromosomal translocation in DLCL, namely, MYC, BCL2 and BCL6, occurring in approximately 10%, 20% and 25% of DLCL respectively, as detected by either cytogenetic or molecular methods (Chaganti, R. S. K., et al., 1991; Rabbits, T. H., 1994; Ladanyi, M., 1991; Offit, K., 1991; Offit, K., 1994). The remaining DLCL exhibit a number of small subsets each characterized by a specific site of recurrent chromosomal rearrangement. The molecular genetic analysis of these sites can contribute significantly to our understanding of the mechanisms of B-cell lymphomagenesis.

One of the recurrent sites of rearrangement seen in 3–4% of DLCL cases is 15q11–13. A notable feature of this site is promiscuity of rearrangement. In addition to translocations involving the immunoglobulin gene sites 14q32 and 22q11, it exhibits translocations with multiple other sites, such as 9p13, 1p32, 7p13, 12q24 and 15q22. Translocations involving 15q11–13 have also been noted in non-lymphoid tumors (Mittelman, F., 1994). The 15q11–13 region has been implicated in genomic imprinting and contains putative genes for human imprinting related disorders such as Prader-Willi and Angelman syndromes. Another unusual feature of the region is the presence of orphan, presumably non-functional, copies of V and D segments of the immunoglobulin heavy chain gene (Tomlinson, I. M., et al., 1994; Wintle, R. F., 1994). The cloning of the t(14:15)(q32;q11–13) breakpoint from a DLCL case and the isolation of a new gene, here named, bcl-8 located at 15q11–13 and potentially involved in the pathogenesis of DLCL is reported.

SUMMARY OF THE INVENTION

This invention provides an isolated nucleic acid which encodes bcl-8.

This invention also provides a vector which includes the isolated nucleic acid which encodes bcl-8 and a host vector system which includes the vector.

This invention also provides a method of producing a polypeptide which comprises growing such a host vector system under suitable conditions permitting the production of the polypeptide and recovering the polypeptide so produced. This invention further provides a method of obtaining purified BCL-8.

This invention further provides the polypeptide encoded by the above-described isolated nucleic acid. Specifically, the invention provides purified BCL-8. In a specific embodiment, the purified BCL-8 is human BCL-8.

This invention also provides an antibody capable of specifically recognizing a polypeptide encoded by bcl-8. This antibody specifically recognizes human BCL-8.

This invention also provides an oligonucleotide of at least 15 nucleotides capable of specifically hybridizing with a sequence of nucleotides within a nucleic acid which encodes bcl-8. This invention also provides an isolated nucleic acid which includes the above-described oligonucleotide.

This invention provides an agent capable of blocking the expression of BCL-8.

This invention provides various methods of determining whether a subject is afflicted with diffuse large cell lymphoma.

This invention also provides various methods of determining whether a subject has a predisposition for diffuse large cell lymphoma.

This invention also provides various methods of treating a subject afflicted with diffuse large cell lymphoma.

This invention also provides various methods of preventing diffuse large cell lymphoma.

This invention also provides various pharmaceutical compositions that prevent diffuse large cell lymphoma in combination with a pharmaceutically acceptable carrier.

Further, this invention also provides various pharmaceutical compositions that treat diffuse large cell lymphoma in combination with a pharmaceutically acceptable carrier.

BRIEF DESCRIPTION OF THE FIGURES

FIGS. 1A–1F. Southern blot analysis of tumor #430 DNA digested with BamHI and HindIII enzymes and hybridized with immunoglobulin heavy chain probes (a–d) and probes located across the chromosomal breakpoints (e,f). Thin arrows point to non-co-migrating $C\mu$ and JH BamHI rearrangement bands. Solid arrows point to co-migrating HindIII rearrangement bands with $C\mu$ and probe A (FIG. 2.I). Open arrows point to co-migrating HindIII rearrangement bands with JH and probe B (FIG. 2.III). The same filter was successively re-hybridized with the different probes.

FIGS. 2-I–2-IV Restriction maps of the deleted immunoglobulin heavy chain allele (I), the normal immunoglobulin heavy chain locus (II), the der(14)t(14;15) (q32;q11–13) translocation allele (III) and the corresponding germline chromosome 15 region (IV). Lines under the maps indicate probes used for Southern and Northern analysis. Open arrow shows the direction of bcl-8 transcription.

subcloned in pBluescript. Left panel: propidium iodide staining of hybridized metaphase. Right panel: G-like banding of the same metaphase revealed by DAPI staining.

FIGS. 4A–4F Somatic cell hybrid mapping of recombinant clones. a–c: BanHI digestion of human/rodent somatic cell hybrids (BIOS Laboratories) hybridized to probe A (FIG. 2.I). d–f: BamHI digestion of monochromosomal cell hybrids containing human chromosomes 14 and 15 (Coriell Cell Repositories) hybridized to probe B (see FIG. 2.III).

Figure 5:
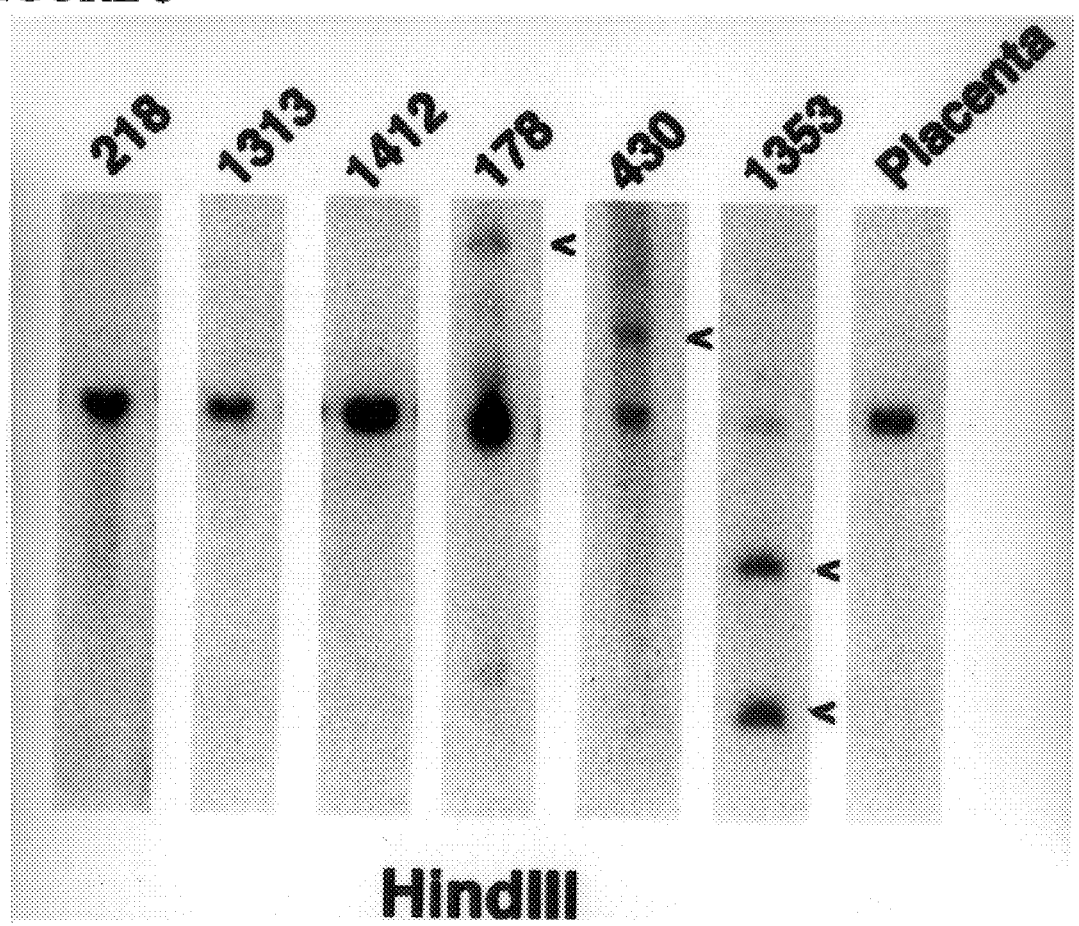

FIG. 5 bcl-8 cDNA map and Northern analysis of BCL-8 expression in human tissues. Open arrows above the map show two alternative transcripts indicated by arrowheads on Northern blots. Probes used in the analysis are indicated by lines under the map. Multiple Tissue Northern blot (Clontech) was successively re-hybridized with all probes.

Figure 6:
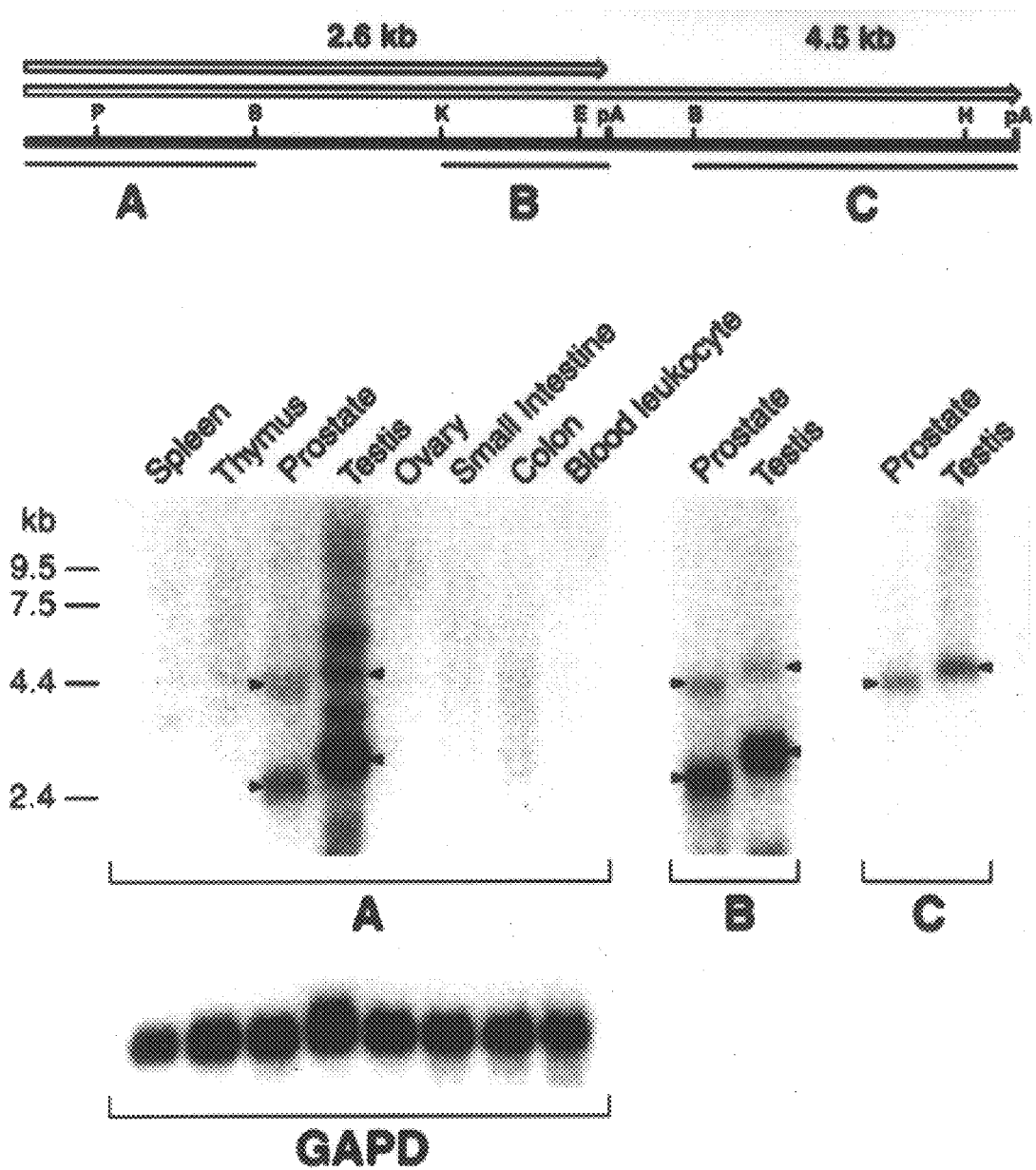

FIG. 6 Southern blot analysis of DLCL DNA using probe B (see FIG. 2.III). Rearrangement bands are indicated with arrowheads.

Figure 7A:
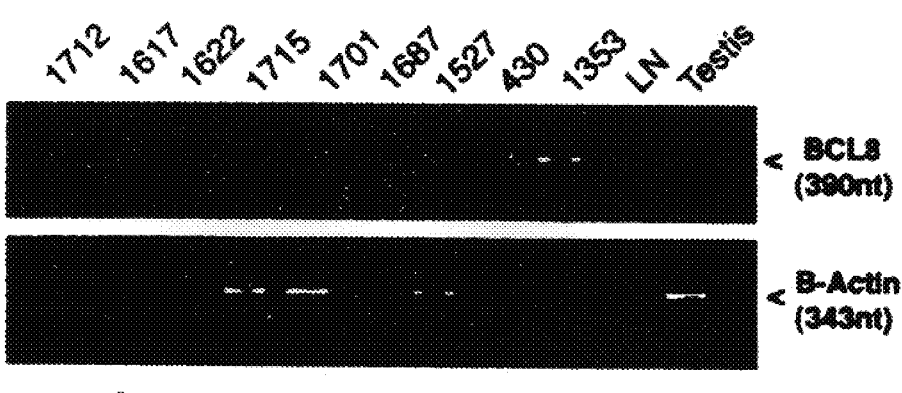
Figure 7B:
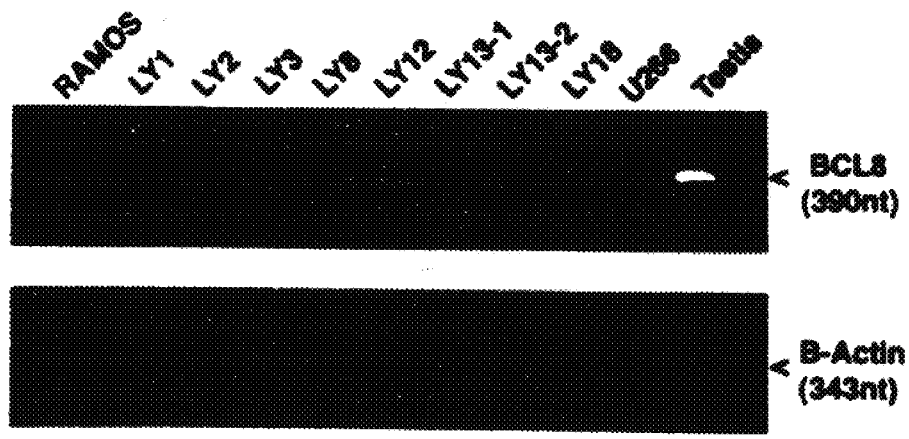

FIGS. 7A–7B RT-PCR analysis of BCL-8 expression in DLCL (a) and lymphoma cell lines (b). Arrowheads indicate bands amplified using bcl-8 specific primers (top) and β-actin primers (bottom). Tumors 1527, 430 and 1353 had translocations affecting 15q11–13. LY numbers represent DLCL cell lines, RAMOS is a Burkitt's lymphoma cell line, U226 is a plasmacytoma cell line and LN is a hyperplastic lymph node with non-malignant proliferation of T- and B-lymphocytes.

FIGS. 8A–8B Nucleic acid sequence of human BCL-8 (SEQ ID NO:3).

FIG. 9 Predicted amino acid sequence of human BCL-8 (SEQ ID NO:4).

DETAILED DESCRIPTION OF THE INVENTION

Throughout this application, references to specific nucleotides are to nucleotides present on the coding strand of the nucleic acid. The following standard abbreviations are used throughout the specification to indicate specific nucleotides:

| | |
|---|---|
| C = cytosine | A = adenosine |
| T = thymidine | G = guanosine |

In order to facilitate an understanding of the Detailed Description, including the Experimental Details, methods and/or terms are described in Sambrook, et al. (1989).

A "gene" means a nucleic acid molecule, the sequence of which includes all the information required for the normal regulated production of a particular protein, including the structural coding sequence, promoters and enhancers.

The nucleic acids and oligonucleotides of the subject invention also include nucleic acids coding for polypeptide analogs, fragments or derivatives of the subject invention which differ from naturally-occurring forms in terms of the identity or location of one or more amino acid residues (deletion analogs containing less than all of the residues specified for the protein, substitution analogs wherein one or more residues specified are replaced by other residues and addition analogs where in one or more amino acid residues is added to a terminal or medial portion of the polypeptides) and which share some or all properties of naturally-occurring forms. These molecules include: the incorporation of codons "preferred" for expression by selected non-mammalian hosts; the provision of sites for cleavage by restriction endonuclease enzymes; and the provision of additional initial, terminal or intermediate DNA sequences that facilitate construction of readily expressed vectors.

The nucleic acids and oligonucleotides described and claimed herein are useful for the information which they provide concerning the amino acid sequence of the polypeptide and as products for the large scale synthesis of the polypeptide by a variety of recombinant techniques. Further the nucleic acids and oligonucleotides are useful for generating new cloning and expression vectors, transformed and transfected prokaryotic and eukaryotic host cells, and new and useful methods for cultured growth of such host cells capable of expression of the polypeptide and related products.

This invention provides an isolated nucleic acid which encodes bcl-8. This isolated nucleic acid may be DNA or RNA, specifically cDNA or genomic DNA. In a specific embodiment, the isolated nucleic acid encodes human bcl-8 having a nucleotide sequence substantially similar to the nucleotide sequence shown in FIG. 8 (Sequence ID No. 3). Further, the isolated nucleic acid encodes bcl-8 having substantially the same amino acid sequence shown in FIG. 9 (Sequence ID No. 4).

As used in this application, "BCL-8" means and includes any polypeptide having BCL-8 activity. Thus, this term includes any such polypeptide whether naturally occuring and obtained by purification from natural sources or non-naturally occurring and obtained synthetically, e.g. by recombinant DNA procedures. Moreover, the term includes any such polypeptide whether its sequence is substantially the same as, or identical to the sequence of any mammalian homolog of the human polypeptide, e.g. murine, bovine, porcine, etc. homologs. Additionally, the term includes mutants or other variants of any of the foregoing which retain at least some of the biological activity of nonmutants or nonvariants.

The invention also encompasses DNAs and cDNAs which encode amino acid sequences which differ from those of bcl-8.

As used herein, "recombinant DNA procedures" include procedures in producing a nucleic acid which does not occur as an individual molecule in nature and which is obtained through the use of recombinant technology.

This invention also provides an isolated nucleic acid encoding bcl-8 operatively linked to a promoter of RNA transcription. Further this invention also provides a vector which comprises the above-described nucleic acid molecule. The promoter may be, or is identical to, a bacterial, yeast, insect or mammalian promoter. Further, the vector may be a plasmid, cosmid, yeast artificial chromosome (YAC), bacteriophage or eukaryotic viral DNA. In a preferred embodiment, this invention provides a vector, specifically a plasmid containing the cDNA sequence for human BCL-8 in a bacterial cell and designated BCL8-P132. BCL8-P132 was made by inserting an isolated nucleic acid encoding human BCL-8 into E. coli by the vector pDR2. BCL8-P132 was deposited on May 23, 1997 with the American Type Culture Collection (ATCC), 10801 University Blvd. Manassas, Va. 20110-2209, U.S.A., under the provisions of the Budapest Treaty For The International Recognition Of The Deposit Of Microorganisms For The Purposes Of Patent Procedure. BCL8-P132 has been accorded ATCC Accession Number 98437.

Other numerous vector backbones known in the art as useful for expressing protein may be employed. Such vectors include, but are not limited to: adenovirus, simian virus 40 (SV40), cytomegalovirus (CMV), mouse mammary tumor virus (MMTV), Moloney murine leukemia virus, DNA delivery systems, i.e. liposomes, and expression plasmid delivery systems. Further, one class of vectors comprises DNA elements derived from viruses such as bovine papilloma virus, polyoma virus, baculovirus, retroviruses or Semliki Forest virus. Such vectors may be obtained commercially or assembled from the sequences described by methods well-known in the art.

This invention also provides a host vector system for the production of a polypeptide which comprises the vector of a suitable host cell. Suitable host cells include, but are not limited to, prokaryotic or eukaryotic cells, e.g. bacterial cells (including gram positive cells), yeast cells, fungal cells, insect cells, and animals cells. Numerous mammalian cells may be used as hosts, including, but not limited to, the mouse fibroblast cell NIH 3T3, CHO cells, HeLa cells, Ltk⁻ cells, Cos cells, etc.

Methods well known in the art, such as calcium phosphate precipitation or electroporation may be otherwise introduced into cells, e.g., by microinjection, may be used to obtain transfected cells.

This invention further provides a method of producing a polypeptide which comprises growing the above-described host vector system under suitable conditions permitting the production of the polypeptide and recovering the polypeptide so produced. Further, this invention provides a method of obtaining a polypeptide in purified form which comprises (a) introducing the vector which includes the isolated nucleic acid encoding bcl-8 in a suitable host cell; (b) culturing the resulting host cell so as to produce the polypeptide; (c) recovering the polypeptide produced in step (b); and (d) purifying the polypeptide so recovered in step (c). As described above, the vector may include a plasmid, cosmid vector, yeast artificial chromosome (YAC), bacteriophage or eukaryotic viral DNA. Also, the host cells may be a bacterial cell (including gram positive cells), yeast cell, fungal cell, insect cell or animal cell. Suitable animal cells include, but are not limited to HeLa cells, Cos cells, CV1 cells and various primary mammalian cells. Culturing methods useful for permitting transformed or transfected host cells to produce polypeptides are well known in the art as are methods for recovering polypeptides from such cells and for purifying the polypeptides.

This invention further provides a purified BCL-8, specifically, wherein the purified BCL-8 is purified human BCL-8.

Methods of recovering polypeptides produced in such host vector systems are well-known in the art and typically include steps involving cell lysis, solubilization and chromatography.

This invention further provides an antibody capable of specifically recognizing a polypeptide encoded by bcl-8. In one embodiment, the polypeptide is a purified BCL-8. In another embodiment, the polypeptide is purified human BCL-8. The antibody may be a monoclonal or polyclonal antibody. Further, the antibody is labeled with a detectable marker that is either a radioactive, colorimetric, fluorescent, or a luminescent marker. The labeled antibody may be a polyclonal or monoclonal antibody. In one embodiment, the labeled antibody is a purified labeled antibody. Methods of labeling antibodies are well known in the art.

The term "antibody" includes, by way of example, both naturally occurring and non-naturally occurring antibodies. Specifically, the term "antibody" includes polyclonal and monoclonal antibodies, and fragments thereof. Furthermore, the term "antibody" includes chimeric antibodies and wholly synthetic antibodies, and fragments thereof.

This invention further provides an oligonucleotide of at least 15 nucleotides capable of specifically hybridizing with a sequence of nucleotides within a nucleic acid which encodes bcl-8. The oligonucleotide may be a DNA or an RNA. Further the oligonucleotide may include a detectable marker, wherein the marker is a radioactive, calorimetric, fluorescent, or a luminescent marker. Specifically, the oligonucleotide includes the sequence of the nucleic acid which encodes bcl-8 linked to a nucleic acid sequence capable of specifically hybridizing with a unique sequence of nucleotides of human chromosome 14. Further the oligonucleotide may have a sequence of a nucleic acid which encodes bcl-8 linked at a specific break point to a specified nucleic acid sequence of human chromosome 14. The specific break point may include a portion of a t(14;15) (q32; q11–13) translocation. The oligonucleotide may be labeled with a detectable marker, wherein the marker is a radioactive, calorimetric, fluorescent, or a luminescent marker.

Further, this invention provides an isolated nucleic acid comprising the above-described oligonucleotide, wherein the nucleic acid is DNA or RNA.

As described here "specifically hybridizing" means the ability of a nucleic acid to recognize only sequences specific to bcl-8.

In one embodiment, one could use the above-described oligonucleotides to probe samples of nucleic acid. Nucleic acid probe technology is well-known to those skilled in the art who will readily appreciate that probes may vary greatly in length, and may be labeled with a detectable label. For example, oligonucleotide or nucleic acid probe molecules may be produced by insertion of an isolated nucleic acid encoding bcl-8 into a suitable vector and transforming the suitable bacterial host cell, replicating the transformed host cell and harvesting the probes using methods well-known in the art. Alternatively, one could synthesize the probes using chemical means.

This invention further provides an agent capable of blocking the expression of the polypeptide encoded by the isolated nucleic acid which encodes bcl-8. The agent may be a triplex oligonucleotide capable of hybridizing to the isolated nucleic acid or an antisense molecule capable of hybridizing to the isolated nucleic acid. Specifically the antisense molecule may be DNA or RNA. Further the agent may be capable of disassociating BCL-8 from naturally binding proteins.

The above-described agent includes, but is not limited to, an inorganic compound, a nucleic acid molecule, an oligonucleotide, an organic compound, a peptide, a peptidomimetic compound, or a protein.

Methods of screening for such agents are well-known in the art such that one skilled in the art could obtain various compounds and screen for those that are capable of blocking the expression of the polypeptide.

This invention further provides a method of determining whether a subject is afflicted with diffuse large cell lymphoma which comprises (a) obtaining an appropriate nucleic acid sample from the B-cells of the subject; and (b) detecting expression of BCL-8 in B-cells of the subject. In one embodiment, the nucleic acid sample in step (a) comprises mRNA corresponding to the transcript of DNA encoding BCL-8 and wherein the detecting of step (b) comprises (i) contacting the mRNA with the above-described oligonucleotides under conditions permitting binding of the mRNA to the oligonucleotide so as to form a complex; (ii) isolating the complex so formed; and (iii) identifying the mRNA in the isolated complex so as to thereby determine whether the mRNA corresponds to the transcript of DNA encoding bcl-8. In a further embodiment, the nucleic acid sample in step (a) comprises mRNA corresponding to the transcript of DNA encoding BCL-8 and the detecting of step (b) comprises (i) amplifying the nucleic acid present in the sample of step (a); and (ii) detecting the presence of bcl-8 in the resulting amplified nucleic acid. One well-known method of amplification is the polymerase chain reaction.

In another embodiment, this invention provides a method of determining whether a subject has diffuse large cell lymphoma which comprises (a) obtaining an appropriate nucleic acid sample from the B-cells of the subject; and (b) detecting in the nucleic acid sample from step (a) a rearrangement of the nucleic acid encoding bcl-8, wherein the rearrangement of the nucleic acid indicates that the subject has diffuse large cell lymphoma. The rearrangement of the nucleic acid encoding bcl-8 may include a translocation of the nucleic acid. One can detect the translocation of the nucleic acid by (i) contacting the nucleic acid sample of step (a) with oligonucleotides containing portions of chromosome 14 or the site of the translocation, e.g. the specific break point, for example t(14;15) (q32;q11–13), under conditions permitting binding of the nucleic acid sample to the oligonucleotide so as to form a complex; (ii) isolating the complex so formed; and (iii) determining whether the nucleic acid sample comprises the sequence of the nucleic acid which encodes bcl-8 linked to a unique sequence of nucleotides included within the sequence of nucleotides of human chromosome 14 or the specific break point.

In order to facilitate isolation of the complexes formed, the oligonucleotide may be labeled with a detectable marker. The detectable marker may be a radioactive isotope, a fluorophor or an enzyme.

This invention further provides a method of determining whether a subject has a predisposition for diffuse large cell lymphoma which comprises (a) obtaining an appropriate nucleic acid sample from the B-cells of the subject; and (b) detecting in the nucleic acid sample from step (a) a rearrangement of the nucleic acid encoding bcl-8, wherein the rearrangement of the nucleic acid indicates that the subject has a predisposition for diffuse large cell lymphoma.

In a specific embodiment, the rearrangement of the nucleic acid encoding bcl-8 comprises a translocation of the nucleic acid. One can detect the translocation of the nucleic acid by (i) contacting the nucleic acid sample of step (a) with oligonucleotides containing portions of chromosome 14 or the site of the translocation, e.g. the specific break point, for example t(14;15) (q32;q11–13), under conditions permitting binding of the nucleic acid sample to the oligonucleotide so as to form a complex; (ii) isolating the complex so formed; and (iii) determining whether the nucleic acid sample comprises the sequence of the nucleic acid which encodes bcl-8 linked to a unique sequence of nucleotides included within the sequence of nucleotides of human chromosome 14 or the specific break point.

This invention further provides a method of treating a subject afflicted with diffuse large cell lymphoma comprising administering an effective amount of the agent capable of inhibiting the expression of the polypeptide. In a specific embodiment, when the agent is an antisense molecule, the antisense molecule is operatively linked to a suitable regulatory element and introduced to a lymphoma cell.

As used herein "effective amount" means an amount of the agent effective to inhibit either BCL-8 or expression of BCL-8.

This invention also provides a method of treating a subject afflicted with diffuse large cell lymphoma comprising administering an effective amount of the above-described agent.

Instead of administration of an agent, this invention also provides a method of treating a subject afflicted with diffuse large cell lymphoma comprising administering an effective amount of the antibody that inhibits BCL-8. In a specific embodiment, the antibody specifically recognizes purified human BCL-8.

As used herein "effective amount" means an amount of the antibody effective to inhibit BCL-8.

This invention further provides a method of preventing diffuse large cell lymphoma in a subject comprising administering an effective amount of the above-described antibodies. In a specific antibody, the antibody specifically recognizes purified human BCL-8.

This invention further provides a method of preventing diffuse large cell lymphoma in a subject comprising administering an effective amount of the above-described agent. Specifically, the agent may be an antisense molecule capable of hybridizing to the isolated nucleic acid encoding bcl-8.

This invention further provides a method of preventing diffuse large cell lymphoma in a subject comprising administering an effective amount of the above-described agent.

This invention also provides various pharmaceutical composition comprising an amount of the above-described agent effective to prevent diffuse large cell lymphoma and a pharmaceutically acceptable carrier. Specifically, the pharmaceutical composition contains an agent which prevents expression of BCL-8 in B-cells. Another pharmaceutical composition comprises an amount of the above-described antibody effective to prevent diffuse large cell lymphoma and a pharmaceutically acceptable carrier. The above-described antibody may specifically recognize purified human BCL-8. In another pharmaceutical composition, the composition contains an effective amount of the above-described agent so as to prevent diffuse large cell lymphoma and a pharmaceutically acceptable carrier.

As used herein, "pharmaceutical composition" could mean therapeutically effective amounts of polypeptide products of the invention together with suitable diluents, preservatives, solubilizers, emulsifiers, adjuvants and/or carriers useful in SCF therapy. A "therapeutically effective amount" as used herein refers to that amount which provides a therapeutic effect for a given condition and administration regimen. Such compositions are liquids or lyophilized or otherwise dried formulations and include diluents of various buffer content (e.g., Tris-HCl., acetate, phosphate), pH and ionic strength, additives such as albumin or gelatin to prevent absorption to surfaces, detergents (e.g., Tween 20, Tween 80, Pluronic F68, bile acid salts). solubilizing agents (e.g., glycerol, polyethylene glycerol), anti-oxidants (e.g., ascorbic acid, sodium metabisulfite), preservatives (e.g., Thimerosal, benzyl alcohol, parabens), bulking substances or tonicity modifiers (e.g., lactose, mannitol), covalent attachment of polymers such as polyethylene glycol to the protein, complexation with metal ions, or incorporation of the material into or onto particulate preparations of polymeric compounds such as polylactic acid, polglycolic acid, hydrogels, etc, or onto liposomes, microemulsions, micelles, unilamellar or multilamellar vesicles, erythrocyte ghosts, or spheroplasts. Such compositions will influence the physical state, solubility, stability, rate of in vivo release, and rate of in vivo clearance of SCF. The choice of compositions will depend on the physical and chemical properties of the protein having SCF activity. For example, a product derived from a membrane-bound form of SCF may require a formulation containing detergent. Controlled or sustained release compositions include formulation in lipophilic depots (e.g., fatty acids, waxes, oils). Also comprehended by the invention are particulate compositions coated with polymers (e.g., poloxamers or poloxamines) and SCF coupled to antibodies directed against tissue-specific receptors, ligands or antigens or coupled to ligands of tissue-specific receptors. Other embodiments of the compositions of the invention incorporate particulate forms protective coatings, protease inhibitors or permeation enhancers for various routes of administration, including parenteral, pulmonary, nasal and oral.

Further, as used herein "pharmaceutically acceptable carrier" are well known to those skilled in the art and include, but are not limited to, 0.01–0.1M and preferably 0.05M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, chelating agents, inert gases and the like.

This invention also provides various pharmaceutical composition comprising an amount of the above-described agent effective to treat diffuse large cell lymphoma and a pharmaceutically acceptable carrier. Specifically, the agent prevents expression of BCL-8 in B-cells. This pharmaceutical composition also comprises an amount of the above-described antibody effective to treat diffuse large cell lymphoma and a pharmaceutically acceptable carrier. The composition also may contain an amount of the above-described agent effective to treat diffuse large cell lymphoma and a pharmaceutically acceptable carrier.

This invention is illustrated in the Experimental Details section which follows. These sections are set forth to aid in an understanding of the invention but are not intended to, and should not be construed to, limit in any way the invention as set forth in the claims which follow thereafter.

Experimental Details

Material and Methods

Molecular cloning, Southern and Northern blot analysis. A genomic library was constructed from case LL430 in λ GEM-11 phage vector (Promega) by partial Sau3A digestion of tumor DNA. Commercial λ DR2 cDNA library from human testis (Clontech) was used for cDNA cloning. Human immunoglobulin heavy chain probes used for initial Southern blot analysis and for genomic library screening were a 5.5 kb BamHI–HindIII fragment containing the entire JH locus (JH) and a 1.3 kb EcoRI fragment containing first two exons of the mu immunoglobulin heavy chain gene (Cμ). For somatic cell hybrid mapping and Northern analysis, probes from cloned chromosomal breakpoints were generated by subcloning of repeat-free fragments from recombinant phages into pBluescript (Stratagene).

FISH analysis. Phage and plasmid probes were labeled with biotin-14-dUTP and hybridized to metaphase spreads from normal human lymphocytes as previously described (Rao, P. H., et al., 1993). Hybridization signal and corresponding bands were visualized with FITC-conjugated avidin (Oncor) following staining and counterstaining, respectively, with propidium iodide and 4,'6'-diamidino-2-phenylindole.

RT-PCR analysis. Total RNA from frozen tumor specimen and cell lines was isolated by the guanidine-isothiocyanate method using RNAgents kit (Promega). MessageClean (GenHunter) was used for further RNA purification resulting in DNA free RNA preparations. The following primers were used for detection of BCL-8 expression: GTTAAGTC-CTAAAAGTCT (forward) (Sequence ID. No. 1) and TAT-AGGAGTAAAGTCTAC (reverse) (Sequence ID. No. 2). β-actin specific primers were used as a positive control (Ladanyi, M., et al., 1992). Minus RT controls were run for all samples and were negative.

Results

Southern blot analysis of the tumor DNA. Case 430, a DLCL, had a t(14;15)(q32;q11–13) translocation, and did not express a clonal immunoglobulin heavy chain phenotype. Southern blotting analysis of tumor DNA digested with BamHI and HindIII showed clonal rearrangements of both the JH and Cμ regions of the immunoglobulin heavy chain gene (FIGS. 1A–D). The JH and Cμ probes used in this analysis hybridized to the same germline BamHI fragment. The JH and Cμ rearranged bands in the tumor DNA did not co-migrate suggesting that either both alleles of immunoglobulin heavy chain gene underwent non-productive rearrangements, or that the JH and Cμ regions of one allele were separated by a translocation breakpoint. In the latter case, the rearranged JH and Cμ fragments would be expected to represent the two reciprocal junctions (FIGS. 1A, B).

Cloning of the t(14;15) (q32;q11–13) translocation breakpoint. To isolate the chromosomal breakpoint, a genomic library of the tumor DNA partially digested with Sau3A was constructed and screened with the JH and Cμ probes. Clones positive with one probe but negative with the other were selected, mapped (FIG. 2) and partially sequenced. To further confirm that the clones selected represented the original rearranged bands in the tumor, probes from the cloned regions located across the breakpoints were hybridized to genomic Southern blots of tumor DNA. The same rearranged bands as those initially detected by the JH and Cμ probes were identified (FIGS. 1E, F).

Figures 3A, 3B, 3C:
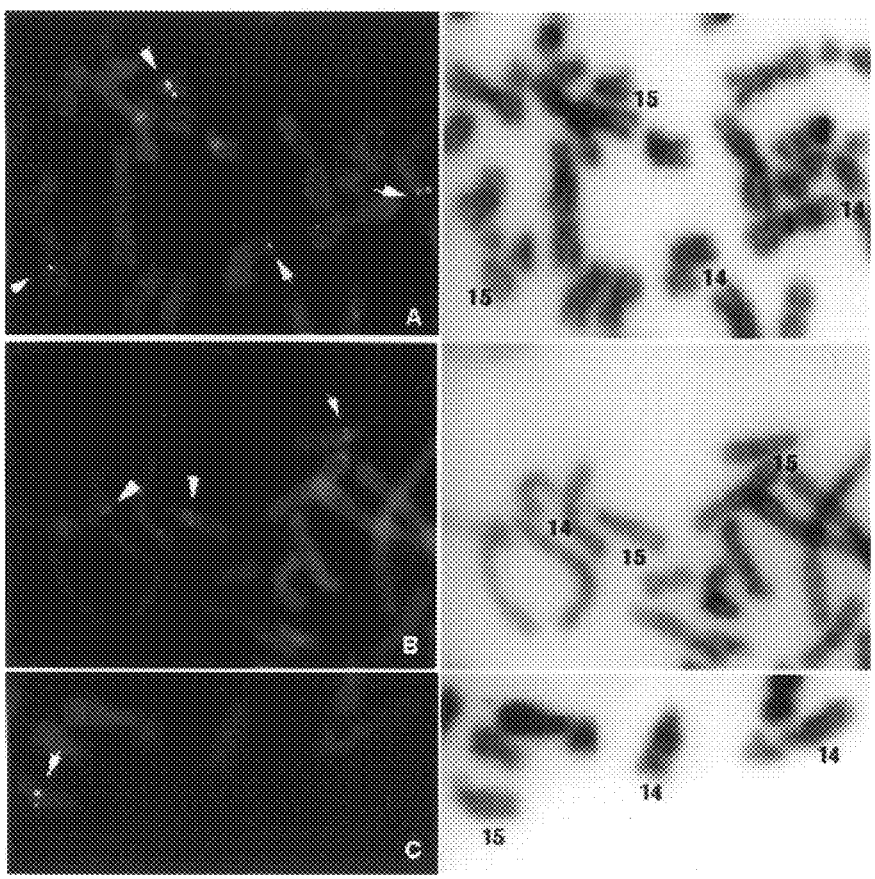
FIGS. 3A–3C FISH mapping of the phages cloned representing the deleted (A) and translocated (B) immunoglobulin heavy chain alleles and the fragment C (see FIG. 2.III)

The Cμ-positive, JH-negative phage clone hybridized to both chromosomes 14 and 15 in FISH analysis suggesting that it may contain the translocation breakpoint (FIG. 3A). A smaller fragment derived from the cloned region (A, FIG. 2.I) also recognized both chromosomes when used as a probe on a panel of somatic cell hybrids yielding four bands on chromosome 14 and a single band on chromosome 15 (FIGS. 4A–C). Partial sequencing of the 5' end of the phage revealed 80% to 90% homology with the D regions of immunoglobulin heavy chain gene. Previously, four D clusters (D1–D4) were shown to be tandemly located at 14q32, 23 kb telomeric to JH and one (D5) was mapped to 15q11–13 (Tomlinson, I. M., et al., 1994; Wintle R. F., et al., 1994; Matsuda F., et al., 1988). Since the only sequence data available for all five D clusters were those for Dxp1–Dxp5 segments, the Dxp segment contained in the cloned region was located and sequenced to determine its chromosomal origin. The sequence was identical to Dxp2. The order of the D segments in the cloned fragment was also consistent with that of D1–D4 clusters but not with that of D5. Based on these data, it was concluded that the cloned phage contained parts of D2 and D3 clusters from chromosome 14 which cross-hybridized with the D5 cluster sequences located on chromosome 15, as well as with other D clusters on chromosome 14. The Cµ-positive, JH-negative rearranged band, therefore, represented a microdeletion in one of the immunoglobulin heavy chain alleles, and was not involved in the t(14;15) translocation.

Since part of one immunoglobulin heavy chain allele, including the JH region, was deleted, the JH-rearranged BamHI band identified in the Southern blot analysis of tumor DNA was not reciprocal to the Cµ-rearranged band. It was considered to originate from the second immunoglobulin heavy chain allele, possibly linked to chromosome 15 by translocation. The fact that both immunoglobulin heavy chain alleles were affected by non-productive rearrangements was consistent with the lack of clonal immunoglobulin heavy chain expression by the tumor. JH-positive, Cµ-negative clones obtained from the genomic library also hybridized to both chromosomes 14 and 15 by FISH (FIG. 3B) and somatic cell hybrid mapping (FIGS. 4D–F). Restriction mapping and partial sequencing revealed immunoglobulin heavy chain-related sequences both 3' and immediately 5' of JH (FIG. 2-III). epsilon immunoglobulin heavy chain gene (Cε) and ε-switch sequences were identified 3' of the JH region. V-related sequences were found 5' of JH. Both JH and Cε regions contained multiple deletions and point mutations, the JH region showing only 80% homology with the germline sequence. The immunoglobulin heavy chain enhancer region was retained in the cloned fragment as confirmed by sequencing. The cloned V-related fragment had 60–70% homology with a number of previously sequenced V regions of immunoglobulin heavy chain gene suggesting that it either originated from a germline V segment that has previously not been sequenced or that it has been altered by deletions and mutations, as was the case with the adjacent JH. Since some V genes have been mapped to 15q11–13 (Tomlinson, I. M., et al., 1994; Wintle, R. F., et al., 1994), this fragment may have originated from either chromosomes 14 or 15. The fragment from the 5' end of the cloned region (Fragments B and C; FIG. 2-III) did not show significant homology to immunoglobulin heavy chain gene or any other sequence in the database and hybridized to chromosome 15 alone in somatic cell hybrids (FIGS. 4D–F) as well as in FISH analysis (FIG. 3C). These data thus demonstrated that this allele was involved in a translocation with a previously unknown sequence on chromosome 15.

bcl -8 transcriptional unit. The germline chromosome 15 region (FIG. 2-IV) was cloned using probe B (FIG. 2-III) to screen a genomic library. Overlapping phage clones spanning the breakpoint area and flanking regions were mapped and partially sequenced. To identify a possible transcriptional unit, a series of probes were derived from the region and hybridized to human multiple tissue Northern blots. Probe C (FIG. 2-IV) detected a 4.5 kb transcript with abundant expression in prostate and testis but not in lymphoid tissues such as thymus, spleen and blood leukocytes.

Cloning of the bcl-8 cDNA. Probe C was used to screen a human testis cDNA library. Restriction mapping and sequence alignment of clones obtained showed that the sequence homologous to probe C was located at the 3' end of the cDNA. cDNA clones with two different 3' ends were found. This was confirmed by preliminary analysis of the cDNA sequence which revealed two potential sites of polyadenylation resulting in two possible transcripts, 2.6 kb and 4.5 kb in size. Using BLAST program no significant homology was found with any DNA sequence other than an EST cloned from human brain cDNA library. The direction of transcription on chromosome 15 was from telomere to centromere. The breakpoint in case #430 was located 3' of the gene bringing the intact gene to the proximity of the retained immunoglobulin heavy chain enhancer which is capable of activating it across the rearrangement junction (FIG. 2).

Analysis of BCL8 splicing variants. The analysis of BCL8 splicing variants revealed a cDNA species of a significantly larger size than the one previously described. The alternatively spliced transcript is expressed not only in testis and prostate but also in other tissues such as brain, spleen and kidney. The size estimated by Northern blot analysis is in the range of 10–11 knt. cDNA clones corresponding to the large transcript have been isolated from human spleen cDNA library. The analysis of these clones is now being completed. Preliminary sequence analysis showed that the alternative transcript contains exons 2–5 but has 5'-end and 3'-end different from the original species. It has an open reading frame of at least 8 knt that overlaps with the previously described open reading frame. The newly cloned 3'-terminal exons showed homology to a number of human ESTs and to CDC4-related gene—a partially cloned human gene with unknown function. At the protein level the previously reported homology with C. elegans protein F10.F2.1 extends into alternative exons both 3' and 5'. In addition to this homology BLAST analysis revealed high homology of the entire predicted protein to the product of a recently cloned gene DAKAP550—a Drosophila A kinase anchoring protein. Other homologies are limited to the carboxy terminus of the protein and include mouse BG gene and it's human analog as well as human and mouse FAN genes and yeast YCR601 gene product.

Northern blot analysis of BCL-8. To verify that both types of bcl-8 transcripts with alternative polyadenylation are expressed in human tissues, cDNA probes were used for Northern analysis. As expected from the cDNA map, the 3' terminal probe C detected only the 4.5 kb transcript, while the 5' terminal probe A and probe B located upstream of the internal polyadenylation site recognized both RNA species. The 2.6 kb transcript appeared to be expressed more abundantly than the 4.5 kb species when detected with these probes. The sizes of the transcripts detected in prostate are consistently smaller than those in the testis. This may indicate alternative splicing and/or an alternative promoter in this tissue. Additional 3.7 kb and 6 kb bands hybridizing to probe A are not consistent with the cDNA map and may indicate the existence of cross-hybridizing, related genes expressed in testis only (FIG. 6). On a multiple species Southern blot, cDNA probes detected strong bands in human and monkey lanes. Detectable bands were also observed across the panel of species including yeast, indicating phylogenetic conservation of the cDNA sequence.

bcl-8 rearrangements in DLCL. To determine whether translocation breakpoints in other DLCL cases cluster within the same region on chromosome 15, a panel of DLCL DNAs was screened by Southern blotting for clonal rearrangements using probe B (FIG. 2-III). Three out of 71 tumor DNAs showed clonal rearrangement within 5 kb of bcl-8 locus (FIG. 5). The frequency of bcl-8 DNA rearrangement was in agreement with that of chromosomal translocations involving 15q11–13.

RT-PCR analysis of BCL-8 expression in lymphomas. To detect BCL-8 expression in RNA extracted from frozen tumor specimen by RT-PCR, primers were designed within the 2.6 kb transcript upstream of the internal polyadenylation site. The primers specifically amplified a 390 nt fragment from human testis RNA. In all tested tumors carrying 15q11–13 abnormalities, an expected 390 bp band was detected. BCL-8 expression was also detectable in 4 out of 9 randomly selected DLCL but in none of the 3 tested hyperplastic lymph nodes (FIG. 7A). To test the possibility that the recognized bands originated from contamination of the tumor tissues with non-lymphoid cells that may normally express BCL-8, a panel of DLCL cell lines was also studied. Six of 15 cell lines without 15q11–13 rearrangements were also positive for BCL-8 expression while a B-lymphoblastoid cell line was negative (FIG. 7B). These data clearly demonstrate ectopic activation in bcl-8 in DLCL.

Discussion

DLCL is a clinically important subset of non-Hodgkin's lymphoma that is highly heterogeneous both at the cytogenetic and molecular levels. The most frequent recurrent translocations in DLCL, so far identified, are t(3;14), t(14;18) and t(8;14), which together are seen in approximately 55% of cases (Ladanyi, M., et al., 1991; Offit, K., et al., 1994). Cytogenetic analysis over the past 10 years has revealed several new recurrent chromosomal sites which translocate with the immunoglobulin gene sites in DLCL, suggesting deregulation of hitherto unidentified genes in the etiology of this disorder. Several of these sites including 15q11–13 exhibit promiscuity in rearrangement; i.e., they participate in recurring translocations involving immunoglobulin genes as well as other chromosomal sites suggesting that the candidate genes at these sites may be deregulated by formation of chimeric gene products, by utilization of unrelated promoters, or by other mechanisms.

Orphan V and D segments with unknown function have previously been mapped to 15q11–13 (Tomlinson, I. M., et al., 1994; Wintle, R. F., et al., 1994). It is possible that the V/D segments on chromosome 15 can rearrange with D/J segments on chromosome 14 resulting in interchromosomally rearranged immunoglublin heavy chain genes. Such a rearrangement would be detectable cytogenetically as t(14;15) (q32;q11–13). In case #430, although the chromosomal origin of the V-related sequence found in the translocated allele is not clear, it is not located immediately downstream of bcl-8 on the germline chromosome 15. It is considered more likely to be of chromosome 14 origin; thus both V-D and D-J recombinations in this tumor may have involved only partners from chromosome 14.

The genomic region of BCL-8 located at 15q11–13 has been identified and cloned which is a recurrent site of rearrangements in a fraction of DLCL. The results of Southern blot analysis of randomly selected DLCLs indicated that BCL-8 rearrangements may account for a significant part of all cytogenetically detectable 15qll–13 abnormalities.

The bcl-8 region contains a transcriptional unit which is not normally expressed in lymphoid tissues. The sequence of the gene has been conserved throughout evolution suggesting its functional significance. So far, there is no direct evidence pointing to the possible function of bcl-8 such as a sequence homology with a gene coding a known protein. RT-PCR analysis of the gene expression in lymphomas, however, showed that BCL-8 is frequently expressed in DLCL being the only known gene so far to be ectopically activated in lymphomas. These data suggest that BCL-8 may play an important role in the pathogenesis of DLCL.

In tumor #430, the most likely mechanism of bcl-8 deregulation is through its juxtaposition to the immunoglobulin heavy chain enhancer located immediately downstream of JH and retained in the translocated allele. Similar mechanisms of activation by a regulatory element across the translocation breakpoint have previously been reported for t(8;14) and t(14;18) (Chaganti, R. S. K., et al., 1991; Rabbits, T. H., 1994). The same mechanism may apply to other cases with 15q11–13 translocations involving sites for the immunoglobulin heavy chain genes 14q32 and 22q11 and possibly some of the unknown rearrangement partners. However, the RT-PCR analysis showed BCL-8 expression in a significant proportion of DLCL including those without cytogenetically detectable 15q11–13 abnormalities. Therefore mechanisms of activation other than translocations such as mutations in regulatory region or deregulation by a trans-acting factor also have to be considered (Dalla-Favera, R., et al., 1994). One of the possible mechanisms includes gene deregulation by changes in the imprinting pattern of the entire chromosomal region which has been shown to contain multiple imprinted genes (Ledbetter, D. H., et al., 1995; Dittrich, B., et al., 1996).

In summary, the cloning of a new gene is reported, bcl-8, which is activated by chromosomal rearrangement in B-cell DLCL, thereby enhancing understanding of the molecular mechanisms of this genetically heterogenous and clinically important group of human B-cell lymphomas. Although its function is yet unknown, it is the first known frequently activated gene in DLCL whose normal expression is not constitutive to normal B-cells.

References

1. Chaganti, R. S. K., Klein, E. A. (1991) in *Molecular Genetics in Cancer Diagnosis,* ed. Cossman, J. (Elsevier, N.Y.), pp73–101.
2. Dalla-Favera, R., Ye, B. H., Lo Coco, F., Gaidano, G., Lista, F., Knowels, D. M., Louie, D. C., Offit, K., Chaganti, R. S. K. (1994) *Cold Spring Harbor Symp Quant Biol.,* 59, 117–123.
3. Dittrich, B., Korn, B., Rickard, S., Buxton, J., Saitoh, S., Nichols, R. D., Poustka, A., Winterpacht, A., Zabel, B., Horsthemke, B. (1996) *Nature Genet.,* 14, 163–170.
4. Ledbetter, D. H., Engel, E. (1995) *Hum. Mol. Genet.,* 4, 1757–1764.
5. Ladanyi, M., Offit, K., Jhanwar, S. C., Filippa, D. A., Chaganti, R. S. K. (1991) *Blood* 77, 1057–1063.
6. Ladanyi, M., Wang, S. (1992) *Diag. Mol. Path.,* 1, 31–35.
7. Magrath, I., (1989) in *The non-Hodgkin lymphoma,* ed. Magrath, I. (Williams & Wilkins, Baltimore), pp29–48.
8. Matsuda, F., Lee, K. H., Nakai, S., Sato, T., Kodaira, M., Zong, S. O., Ohno, H., Fukuhara, S., Honjo, T. (1988) *EMBO J.,* 7, 1047–1051.
9. Mittelman, F. (1994) *Catalog of chromosomal aberrations in cancer,* (Wiley-Liss, New York).
10. Offit, K., Chaganti, R. S. K. (1991): in *Hematology/ oncology clinics of North America. Non-Hodgkin's lymphoma,* ed. Armitage, J. O. (W. B. Saunders, Philadelphia), pp853–869.
11. Offit, K., Lo Coco, F., Louie, D. C., Parsa, N. Z., Leung, D., Portlock, C., Bihui, H. Y., Lista, F., Filippa, D. A., Rosenbaum, A., Ladanyi, M., Jhanwar, S., Dalla-Favera, R., Chaganti, R. S. K. (1994) *New England J. Med.* 331, 74–80.
12. Rabbits, T. H. (1994) *Nature* 372, 143–149.
13. Rao, P. H., Murty, V. V. V. S., Gaidano, G., Hauptschein, R., Dalla-Favera, R., Chaganti, R. S. K. (1993) *Genomics* 16, .426–430.
14. Simon, R., Durrleman, S., Hoppe, R. T., Bonadonna, G., Bloomfield, C. D., Rudders, R. A., Cheson, B. D., Berard, C. W. (1988) *Ann. Intern. Med.* 109, 939–945.
15. Tomlinson, I. M., Cook, G. P., Carter, N. P., Elaswarapu, R., Smith, S., Walter, G., Buluwela, 1., Rabbits, T. H., Winter, G. (1994) *Hum. Mol. Genet.* 3, 853–860.
16. Wintle, R. F., Cox, D. W. (1994) *Genomics* 23, 151–157.

EQUENCE LISTING

<160> NUMBER OF SEQ ID NOS: 4

<210> SEQ ID NO 1
<211> LENGTH: 18
<212> TYPE: DNA
<213> ORGANISM: nucleic acid: synthesized

<400> SEQUENCE: 1
gttaagtcct aaaagtct                                                        18

<210> SEQ ID NO 2
<211> LENGTH: 18
<212> TYPE: DNA
<213> ORGANISM: nucleic acid: synthesized

<400> SEQUENCE: 2
tataggagta aagtctac                                                        18

<210> SEQ ID NO 3
<211> LENGTH: 2340
<212> TYPE: DNA
<213> ORGANISM: human

<400> SEQUENCE: 3

| | | | | | | |
|---|---|---|---|---|---|---|
| accactatac | ggctcgagcg | gccgcccggg | caggtctgta | ctttacatgc | agtgctactc | 60 |
| tttcggcatt | cctggttgaa | ctacttaaaa | gttcagtagc | catgcaagaa | caggtgctgg | 120 |
| gtggaaaacg | cttttagtt  | attggctatt | tacttgaaaa | gtcatcaaga | gttcatataa | 180 |
| ctagacctgt | cttggagcaa | ttttatctt  | ttgcaaaata | ccttgatggt | ttatctcatg | 240 |
| gagcaccttt | gctgaagcag | ctttgtgatc | atatttgtt  | tattaaccca | gccatctgga | 300 |
| tacatacacc | tgcaaaggtt | caactttccc | tatatacata | tttgtctgct | gaatttattg | 360 |
| gaactgctac | catctacacc | accatacgca | gaataggaca | gttattaaag | ataatgcaca | 420 |
| ccttaaaata | ttactactgg | gttattaatc | ctgctgacag | tagcggcatt | acacctaaag | 480 |
| gattagagcc | aaagattcct | gaagacagag | ctgatgccat | gtactcaagt | gggtctctgc | 540 |
| ctctcagagg | tggccttggt | cttcaagttt | cagcaattct | gggaagccaa | ggacacctcc | 600 |
| atctcctcct | gcctgatctg | caactcatct | gagagcagct | ttctcattgg | aatgtcttgt | 660 |
| gtttaaggaa | caagaatccc | tgtttccggt | ttgggtgccc | aagtgcacct | actggatcca | 720 |
| acccaggatt | ggagatactt | tgcagaacac | aacatcatct | ggcacatgac | cagccatggt | 780 |
| gtttcacttt | cacaatttca | gcttccttca | ctgatggcag | cataatcgtg | gttcagcagc | 840 |
| ctccaagacc | aggggctggt | gtgggcggct | acagggagaa | attgaagagg | aagttcttgg | 900 |
| tggtgccctc | catgagtaca | aagaagcctc | acagtcccca | ggacacccctt | ccgtgcatgg | 960 |
| tgtcactgac | atctttattt | cttttgtcac | gttctgtaaa | tcacaatgaa | tggggtattc | 1020 |
| ttcttctatt | atatatttgt | taagtctttt | ttggcatctt | taaaaaaaag | tggtaactttt | 1080 |
| atcctatgta | atatccctgt | taagtcctaa | aagtcttttc | tgatgtctat | tttgtctgaa | 1140 |
| atttgcacag | ctactatagc | tttatttcgg | ttcatatttt | cataatccat | gttttctcat | 1200 |
| ccttttatat | ttgtgaatgt | gtaaagtaac | tttcttgtgc | atagctaaga | gtttggtctt | 1260 |
| gcttttttaa | atcgactata | agttctattt | ttaaactaat | attttctctt | attttttgtt | 1320 |
| taagatagca | tttcataatg | atgtttattt | ctccattaac | atattaccta | attcacttttt | 1380 |

-continued

```
tataaatatt atatttgtta ccataaggtt tgcaaaagga gcgattcttc attttggaac    1440
cctttcttat tttctgggta ccatgagaaa ttgtagactt tactcctata ttctctttcc    1500
aagccctagg attagccatt tttccaagaa atgttgcata ccattctgct atgaagggaa    1560
ccaaaactca aatcttgatt ctgggtgtat tttttgttaa tttgctgtct tttcttgtag    1620
aacctctcag gtaatgactc taggaggtat gtgttgtgta ttaacccata tatacacaca    1680
catctaaact atttttattt aatttttata cctatattat gctaaacttg caaatatatt    1740
gacacatctg ccctgttaat accacatgaa tgtttattac ctgccttcta ttcctgtccc    1800
taacctcgca ctccaaccgt gaggaacccc ctcctgccac accctgtcta ttccctttgt    1860
agtccagttc caggatttct gtagagtgga accagattgt gtatgttttg ctcttttgtg    1920
gaacatcatc agctggggta cagttctgac gtgcactttc tttattcttt tattgactac    1980
actatttctg aggtcacttg gcacctcttc tgatttcata catttgtaat gacattagat    2040
attttctata ttgtctgcat tctatcctgg aattcctaat ctcctattta tttatatttt    2100
tgtgaattgg aattaaccct ttatgctgta tattctgttg atttcaacaa attcatatca    2160
catatttacc attataatat tatacataat acttccatca ccctttaaa tctattttt     2220 acccattttc atcatctcct taaatttctc gcaaatacag aatcactttg tgtgtttgga    2280
cttctccaga atatcaaata aataacatat tatgtagctt tttcagactt gtttctttca    2340
```

<210> SEQ ID NO 4
<211> LENGTH: 176
<212> TYPE: PRT
<213> ORGANISM: human

<400> SEQUENCE: 4

```
Met Gln Glu Gln Val Leu Gly Gly Lys Arg Phe Leu Val Ile Gly Tyr
  1               5                  10                  15

Leu Leu Glu Lys Ser Ser Arg Val His Ile Thr Arg Pro Val Leu Glu
                 20                  25                  30

Gln Phe Leu Ser Phe Ala Lys Tyr Leu Asp Gly Leu Ser His Gly Ala
             35                  40                  45

Pro Leu Leu Lys Gln Leu Cys Asp His Ile Leu Phe Ile Asn Pro Ala
         50                  55                  60

Ile Trp Ile His Thr Pro Ala Lys Val Gln Leu Ser Leu Tyr Thr Tyr
 65                  70                  75                  80

Leu Ser Ala Glu Phe Ile Gly Thr Ala Thr Ile Tyr Thr Thr Ile Arg
                 85                  90                  95

Arg Ile Gly Gln Leu Leu Lys Ile Met His Thr Leu Lys Tyr Tyr Tyr
                100                 105                 110

Trp Val Ile Asn Pro Ala Asp Ser Ser Gly Ile Thr Pro Lys Gly Leu
            115                 120                 125

Glu Pro Lys Ile Pro Glu Asp Arg Ala Asp Ala Met Tyr Ser Ser Gly
        130                 135                 140

Ser Leu Pro Leu Arg Gly Gly Gly Leu Gln Val Ser Ala Ile Leu
145                 150                 155                 160

Gly Ser Gln Gly His Leu His Leu Leu Leu Pro Asp Leu Gln Leu Ile
                165                 170                 175
```

What is claimed is:

1. An isolated nucleic acid which encodes a protein having the amino acid sequence set forth in FIG. 9 (SEQ ID NO:4).

2. The isolated nucleic acid of claim 1, wherein the nucleic acid is DNA.

3. The isolated nucleic acid of claim 1, wherein the nucleic acid is RNA.

4. The isolated nucleic acid of claim 1, wherein the nucleic acid has the nucleotide sequence set forth in FIG. 8 (Sequence ID No. 3).

5. The isolated nucleic acid of claim 1, operatively linked to a promoter of RNA transcription.

6. A vector which comprises the nucleic acid of claim 5.

7. The vector of claim 6, wherein the promoter is a bacterial, yeast, insect or mammalian promoter.

8. The vector of claim 6, wherein the vector is a plasmid, cosmid, yeast artificial chromosome (YAC), bacteriophage or eukaryotic viral DNA.

9. A host vector system for the production of a polypeptide which comprises the vector of claim 6, in a suitable host cell.

10. The host vector system of claim 9, wherein the suitable host cell is a prokaryotic or eukaryotic cell.

11. The host vector system of claim 10, wherein the prokaryotic cell is a bacterial cell.

12. The bacterial cell designated BCL8-P132 and deposited under ATCC Accession No. 98437.

13. The host vector system of claim 10, wherein the eukaryotic cell is a yeast cell, insect cell, plant cell or mammalian cell.

14. A method of producing a polypeptide which comprises growing the host vector system of claim 9 under conditions permitting the production of the polypeptide encoded by the vector therein, and recovering the polypeptide so produced.

15. A method of obtaining a polypeptide in purified form which comprises:

(a) introducing the vector of claim 6 into a suitable host cell;

(b) culturing the resulting host cell so as to produce the polypeptide encoded by the vector therein;

(c) recovering the polypeptide produced in step (b); and (d) purifying the polypeptide so recovered in step (c).

* * * * *